US012434009B2

(12) United States Patent
Säll

(10) Patent No.: US 12,434,009 B2
(45) Date of Patent: Oct. 7, 2025

(54) ASSEMBLY FOR A MEDICAMENT DELIVERY DEVICE

(71) Applicant: SHL MEDICAL AG, Zug (CH)

(72) Inventor: Daniel Säll, Segeltorp (SE)

(73) Assignee: SHL Medical AG, Zug (CH)

(*) Notice: Subject to any disclaimer, the term of this patent is extended or adjusted under 35 U.S.C. 154(b) by 874 days.

(21) Appl. No.: 17/553,142

(22) Filed: Dec. 16, 2021

(65) Prior Publication Data

US 2022/0257871 A1 Aug. 18, 2022

(30) Foreign Application Priority Data

Feb. 15, 2021 (EP) .................................... 21157206

(51) Int. Cl.
*A61M 5/315* (2006.01)

(52) U.S. Cl.
CPC ............................... *A61M 5/31585* (2013.01)

(58) Field of Classification Search
CPC .............. A61M 5/31585; A61M 5/145; A61M 5/14244; A61M 5/14248
See application file for complete search history.

(56) References Cited

U.S. PATENT DOCUMENTS 6,613,017 B1 9/2003 Mickley
7,297,136 B2 11/2007 Wyrick
7,678,077 B2 3/2010 Harris et al.
8,206,351 B2 6/2012 Sugimoto et al.
9,180,252 B2 * 11/2015 Gelblum ............. A61M 5/2425
9,327,085 B2 5/2016 Jackson et al.
9,539,139 B2 1/2017 Andino et al.
9,737,663 B2 8/2017 Jennings et al.
10,384,019 B2 8/2019 Raylman
2008/0097319 A1 * 4/2008 Shih ...................... A61M 5/148 604/131
2009/0259180 A1 10/2009 Choi
(Continued)

FOREIGN PATENT DOCUMENTS

CN 105833396 A 8/2016
CN 109498909 A 3/2019
GB 2461732 A 1/2010
(Continued)

*Primary Examiner* — Dung T Ulsh
(74) *Attorney, Agent, or Firm* — McDonnell Boehnen Hulbert & Berghoff LLP

(57) ABSTRACT

An assembly for a medicament delivery device is presented having a container holder with a body extending along a longitudinal axis between a proximal and a distal end, the body defining an interior chamber for receiving a medicament container. An actuator is connected to the container holder and axially movable relative to the body of the container holder. The drive assembly is attached to the body of the container holder has a motion converter and a rod, where the actuator has an activation surface movable relative to the motion converter of the drive assembly in the direction of the longitudinal axis such that a movement of the actuator relative to the container holder in the direction of the longitudinal axis is converted to a movement of the rod relative to the container holder along a transverse axis transverse to the longitudinal axis through an engagement between the motion converter of the drive assembly and the activation surface of the actuator.

13 Claims, 9 Drawing Sheets

(56) References Cited

U.S. PATENT DOCUMENTS

2018/0363638 A1* 12/2018 Holzhausen ...... A61M 5/14232

FOREIGN PATENT DOCUMENTS

| | | | |
|---|---|---|---|
| WO | 2011/034576 | A1 | 3/2011 |
| WO | 2011/094025 | A1 | 8/2011 |
| WO | 2011/109840 | A2 | 9/2011 |
| WO | 2016/186965 | A2 | 11/2016 |
| WO | 2019/238825 | A1 | 12/2019 |

* cited by examiner

ASSEMBLY FOR A MEDICAMENT DELIVERY DEVICE

CROSS REFERENCE TO RELATED APPLICATIONS

The present application claims priority to European Patent Application No. 21157206.0 filed Feb. 15, 2021 which is herewith incorporated by reference into the present application.

TECHNICAL FIELD

The present disclosure generally relates to an assembly for a medicament delivery device and particularly to an assembly with a drive assembly comprising a rod and a motion converter.

BACKGROUND

Medicament delivery devices such as pen-type injectors or safety syringes are generally known for the self-administration of a medicament by patients without formal medical training. As just one example, those patients suffering from diabetes may require repeated injections of insulin. Other patients may require regular injections of other types of medicaments, such as a growth hormone.

To help patients perform the self-administration of a medicament, medicament delivery devices are usually designed with one or more assemblies or sub-assemblies providing automatic functions, force transferring functions, and/or manipulation guide functions. The medicament can therefore be prepared properly, applied with a proper force and/or be delivered within a proper time period without any complicated manipulation by patients.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal" and "longitudinally" refer to a direction extending from the proximal end to the distal end, typically along with the device or components thereof in the direction of the longest extension of the device and/or component.

Similarly, the terms "transverse", "transversal" and "transversally" refer to a direction generally perpendicular to the longitudinal direction.

Further, the terms "circumference", "circumferential", "circumferentially", "radial", "radially", "rotation", "rotational" and "rotationally" refer to a direction generally perpendicular to the longitudinal direction and at least partially extending around the longitudinal direction.

There is hence provided an assembly for a medicament delivery device, the assembly comprising: a container holder comprising a body extending along a longitudinal axis between a proximal and a distal end, the body defining an interior chamber for receiving a medicament container; an actuator connected to the container holder and axially movable relative to the body of the container holder; and a drive assembly attached to the body of the container holder; wherein the drive assembly comprises a motion converter and a rod; wherein the actuator comprises an activation surface movable relative to the motion converter of the drive assembly in the direction of the longitudinal axis; and wherein a movement of the actuator relative to the container holder in the direction of the longitudinal axis is converted to a movement of the rod relative to the container holder along a transverse axis transverse to the longitudinal axis through an engagement between the motion converter of the drive assembly and the activation surface of the actuator.

According to one embodiment, the motion converter of the drive assembly is attached to the rod.

According to one embodiment, the motion converter of the drive assembly comprises an inclined surface angled to the transverse axis and the longitudinal axis.

According to one embodiment, the activation surface of the actuator comprises an inclined surface angled relative to the transverse axis and the longitudinal axis.

According to one embodiment, the inclined surface of the motion converter of the drive assembly is configured to face towards the inclined surface of the activation surface of the actuator.

According to one embodiment, the motion converter of the drive assembly comprises a protrusion extending from the body of the container holder in the direction of the transverse axis.

According to one embodiment, the motion converter of the drive assembly comprises a rotator fixed to the body of the container holder in the direction of the transverse axis and rotatable around the transverse axis relative to the body of the container holder; and the rotator comprises a body comprising an outer surface.

According to one embodiment, the activation surface of the actuator comprises a protrusion.

According to one embodiment, the protrusion of the activation surface of the actuator extends in the direction of the longitudinal axis.

According to one embodiment, the rotator comprises a guide track on the outer surface of the body of the rotator; the protrusion of the activation surface of the actuator extends in a direction perpendicular to the longitudinal axis; and the protrusion of the activation surface of the actuator follows the track of the rotator when the actuator moves relative to the rotator in the direction of the longitudinal axis.

According to one embodiment, the rotator comprises teeth extending outwardly relative to the transverse axis from the outer surface of the body of the rotator; the activation surface of the actuator comprises a rack; each tooth of the rack extends in a direction perpendicular to the longitudinal axis; and the rack aligns with the teeth of the rotator in the direction of the longitudinal axis.

According to one embodiment, the rotator comprises an engaging member on a surface of the body of the rotator; the rod comprises a first engaging member engaged with the engaging member of the rotator thereby defining a first interface; the rod comprises a second engaging member engaged with a counter engaging member of the body of the container holder thereby defining a second interface; and one of the first interface and the second interface is a helical interface; and the other one of the first interface and the second interface is a spline interface.

According to one embodiment, the first interface is a helical interface.

According to one embodiment, the first engaging member of the rod is a helical thread; and the engaging member of the rotator is a protrusion.

According to one embodiment, the first engaging member of the rod is a protrusion; and the engaging member of the rotator is a helical thread.

According to one embodiment, the second engaging member of the rod is a rib.

According to one embodiment, the second engaging member of the rod is a slot.

According to one embodiment, the counter engaging member arranged on the body of the container holder is a rib.

According to one embodiment, the counter engaging member arranged on the body of the container holder is a slot.

According to one embodiment, the second interface is a helical engagement.

According to one embodiment, the second engaging member of the rod is a helical thread; and the counter engaging member of the body of the container holder is a protrusion.

According to one embodiment, the second engaging member of the rod is a protrusion; and the counter engaging member of the body of the container holder is a helical thread.

According to one embodiment, the first engaging member of the rod is a rib.

According to one embodiment, the first engaging member of the rod is a slot.

According to one embodiment, the engaging member of the rotator is a rib.

According to one embodiment, the engaging member of the rotator is a slot.

According to one embodiment, the body of the rotator is ring-shaped or tubular.

According to one embodiment, the engaging member of the rotator is arranged on an inner surface of the body of the rotator.

According to one embodiment, the rod comprises a rod body extending along the transverse axis According to one embodiment, the body of the rotator at least partially encloses the rod body; and the first engaging member of the rod is arranged on an outer surface of the rod body.

According to one embodiment, the engaging member of the rotator is arranged on the outer surface of the body of the rotator.

According to one embodiment, the rod body comprises a tubular portion at least partially enclosing the body of the rotator; and the first engaging member of the rod is arranged on an inner surface of the tubular portion of the rod body.

According to one embodiment, the second engaging member of the rod is arranged on an outer surface of the rod body.

According to one embodiment, the rod body comprises a tubular portion; and wherein the second engaging member of the rod is arranged on an inner surface of the tubular portion of the rod body.

According to one embodiment, the assembly comprises two drive assemblies aligned parallel to one another on the body of the container holder; the movement of the actuator relative to the container holder in the direction of the longitudinal axis is configured to move sequentially each rod of the two drive assemblies along the transverse axis through the engagements between the two motion converters of the two drive assemblies and the activation surface of the actuator.

According to one embodiment, the assembly comprises two drive assemblies aligned coaxially to one another in the direction of the transverse axis on the body of the container holder; the actuator comprises two activation surfaces; the movement of the actuator relative to the container holder in the direction of the longitudinal axis moves each rod of the two drive assemblies in the direction of the transverse axis through the engagement between one motion converter of the two drive assemblies and one activation surface of the actuator; and the engagement between the other one motion converter of the two drive assemblies and the other one activation surface of the actuator.

According to one embodiment, the rotator is fixed to the body of the container holder in the direction of the longitudinal axis.

According to one embodiment, the assembly comprises a motor connected to the actuator and a switch attached to the container holder; the switch is movable relative to the body of the container holder between an open position and a closed position where the motor is configured to initiate the movement of the actuator relative to the body of the container holder.

According to one embodiment, the switch is movable relative to the body of the container holder between the open position and the closed position along a linear path.

According to one embodiment, the assembly comprises a biasing member being compressible between a relaxed position and a compressed position along the linear path of the switch; the biasing member at least partially surrounds the switch; and a linear moving distance between the relaxed position of the biasing member and the compressed position of the biasing member is longer than a linear moving distance between the open position of the switch and the closed position of the switch.

According to one embodiment, the biasing member is a compression coil spring; and the switch is surrounded by the compression coil spring.

According to one embodiment, the linear path of the switch is in the direction of the longitudinal axis According to one embodiment, the assembly can be operated by a method comprising the steps of: placing a medicament container within the interior chamber of the container holder; moving the actuator along the longitudinal axis relative to the body of the medicament container; moving the rod along the transverse axis relative to the body of the medicament container upon moving the actuator.

According to one embodiment, the step of placing a medicament container within the interior chamber of the container holder further comprises the steps of: inserting the medicament container from the proximal end of the body of the container holder; and moving the medicament container axially along the longitudinal axis towards the distal end of the body of the container holder.

According to one embodiment, the method comprises the step of: moving the switch from the open position to the closed position upon placing a medicament container within the interior chamber of the container holder.

According to one embodiment, the method comprises the step of: compressing the biasing member from the relaxed position to the compressed position upon placing a medicament container within the interior chamber of the container holder; and moving the switch from the open position to the closed position.

According to one embodiment, the assembly can be used in a medicament delivery device.

According to one embodiment, the medicament delivery device that comprises the assembly can be an auto-injector, a pen injector, an inhalation device, or a medical sprayer.

According to one embodiment, the medicament delivery device comprises a collapsible medicament container.

According to one embodiment, the collapsible medicament container is configured to connect to a preassembled medicament delivery member.

According to one embodiment, a fluid connection between the preassembled medicament delivery member and a medicament contained within the collapsible medicament container is configured to be established by a user who will start a medicament delivery operation shortly.

According to one embodiment, the medicament delivery member can be an injection needle, a cannula or a spray nozzle.

According to one embodiment, the medicament delivery device comprises an outer shell extending along the longitudinal axis between a proximal end and a distal end; the container holder is arranged within the outer shell.

According to one embodiment, the actuator is arranged within the outer shell.

According to one embodiment, the medicament delivery device comprises a delivery member guard at least partially arranged within the outer shell; the delivery member guard comprises a tubular body defining a central passage extending along the longitudinal axis, the tubular body is for surrounding a delivery member connected to the medicament container.

According to one embodiment, the delivery member guard comprises two buttons arranged on the tubular body of the delivery member guard and aligned coaxially to one another in the direction of the transverse axis; two buttons are movable relative to the outer shell in the direction of the transverse axis between a relaxed position and a pressed position where the two buttons are closer to each other in the direction of the transverse axis in the pressed position than in the relaxed position.

According to one embodiment, the delivery member guard comprises two biasing elements respectively arranged between each button and the tubular body of the delivery member guard; and the biasing elements are compressible in the direction of the transverse axis between the relaxed position of the two buttons and the pressed position of the two buttons.

According to one embodiment, the biasing elements are compression coil springs.

According to one embodiment, the biasing elements are tension coil springs.

According to one embodiment, the biasing elements are bend springs.

According to one embodiment, the delivery member guard is movable along the longitudinal axis relative to the outer shell between an extended position where the two buttons protrude completely from the proximal end of the outer shell in the direction of the longitudinal axis and a retracted position where the two buttons at least partially received within a proximal portion of the outer shell.

According to one embodiment, a transversely linear distance between the two buttons when the two buttons are in the relaxed position defines a first length; a transversely linear distance between two buttons when the two buttons are in the pressed position defines a second length; and a transversely measured length of the proximal portion of the outer shell is smaller than the first length and greater than the second length.

According to one embodiment of the present disclosure, that provides an assembly for a medicament delivery device comprising: a container holder comprising a body extending along a longitudinal axis between a proximal end and a distal end, the body defining an interior chamber for receiving a medicament container; an actuator movable in the direction of the longitudinal axis relative the body of the container holder; a drive assembly attached to the body of the container holder; the drive assembly comprises a motion converter and a rod movable along a transverse axis transverse to the longitudinal axis relative to the body of the container holder; and the actuator comprises an activation surface configured to interact with the motion converter of the drive assembly when the actuator moves relative to the container holder in the direction of the longitudinal axis so that the rod is moved along the transverse axis.

According to one embodiment of the present disclosure, that provides a method of operating an assembly for a medicament delivery device, the assembly comprising a container holder comprising a body for receiving a medicament container; an actuator movable along a longitudinal axis relative to the body of the container holder; and a drive assembly attached to the body of the container holder; wherein the drive assembly comprises a transversely movable rod and a motion converter; the method comprising the steps of: placing a medicament container within the body of the container holder; moving the actuator along the longitudinal axis relative to the body of the medicament container; moving the rod along the transverse axis relative to the body of the medicament container upon moving the actuator.

Generally, all terms used in the claims are to be interpreted according to their ordinary meaning in the technical field, unless explicitly defined otherwise herein. All references to “a/an/the element, apparatus, component, means, etc.” are to be interpreted openly as referring to at least one instance of the element, apparatus, component, means, etc., unless explicitly stated otherwise.

BRIEF DESCRIPTION OF THE FIGURES

Embodiments of the inventive concept will now be described, by way of example only, with reference to the accompanying drawings, in which.

DETAILED DESCRIPTION

FIGS. 1-10B illustrate an assembly 1 for a medicament delivery device. The assembly 1 comprises a container holder 10 comprising a body 101 that defines an interior chamber 102 for receiving a medicament container. The body extends along a longitudinal axis L between a proximal end and a distal end. The shape of the interior chamber 102 may be dependent on a shape of the medicament container. For example, when the medicament container is elongated, cylindrical or flat, the interior chamber 102 may be formed as correspondingly elongated, cylindrical or flat shaped respectively. Similarly, the body 101 of the container holder 10 may be dependent on a shape of the medicament container as the interior chamber 102. On the other hand, the body 101 of the container holder 10 may be a shape that is different from the shape of the interior chamber 102; for example, the body 101 may be formed as a shape corresponding to the shape of an outer shell of a medicament delivery device that the assembly 1 can be included in said outer shell. Alternatively, the body 101 may be formed as a shape that is easy for a user to grip, so that the user may carry out a medicament delivery operation with the assembly 1.

Figure 2:
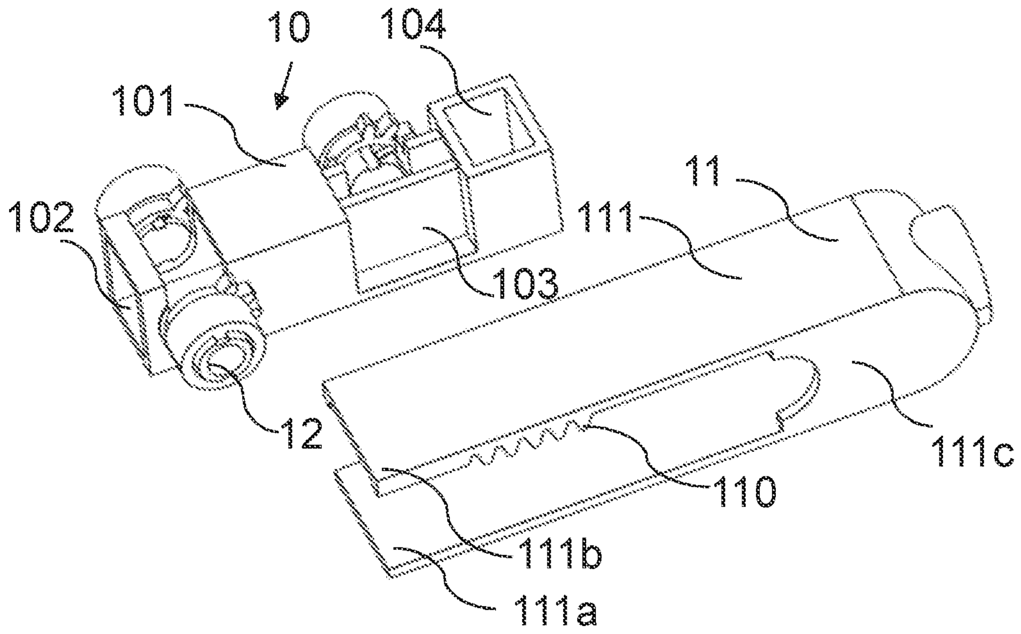
FIG. 2 schematically shows a perspective view of parts of components of the assembly of FIG. 1.

As shown in FIG. 2, the body 101 of the container holder 10 may comprise a retaining portion 103 and a distal partition 104 (will be explained in detail later). The retaining portion 103 is configured to fix or to help to fix a medicament container that will be contained within the body 101 of the container holder 10. In a preferred example, the retaining portion 103 is a part of the body 101 of the container holder 10. The retaining portion 103 may be designed as a shape corresponding with at least a part of a shape of the medicament container that will be contained within the interior chamber 102. For example, if the medicament container is formed as generally cylindrical shape, the retaining portion 103 can be formed as a generally cylindrical shape; or if the medicament container comprises a flat portion, the retaining portion 103 can be formed with a diameter being narrower than a diameter of the rest of the interior chamber 102 of the container holder 10, so that the retaining portion 103 can snugly receive the flat portion of the medicament container.

The retaining portion 103 may be configured to press-fit with the medicament container, or the retaining portion 103 may comprise a pair of flexible arms for snap fitting with the medicament container. Alternatively, the retaining portion 103 may function together with another component to clamp or fix the medicament container to the interior chamber 102 of the medicament delivery device.

Figure 1:
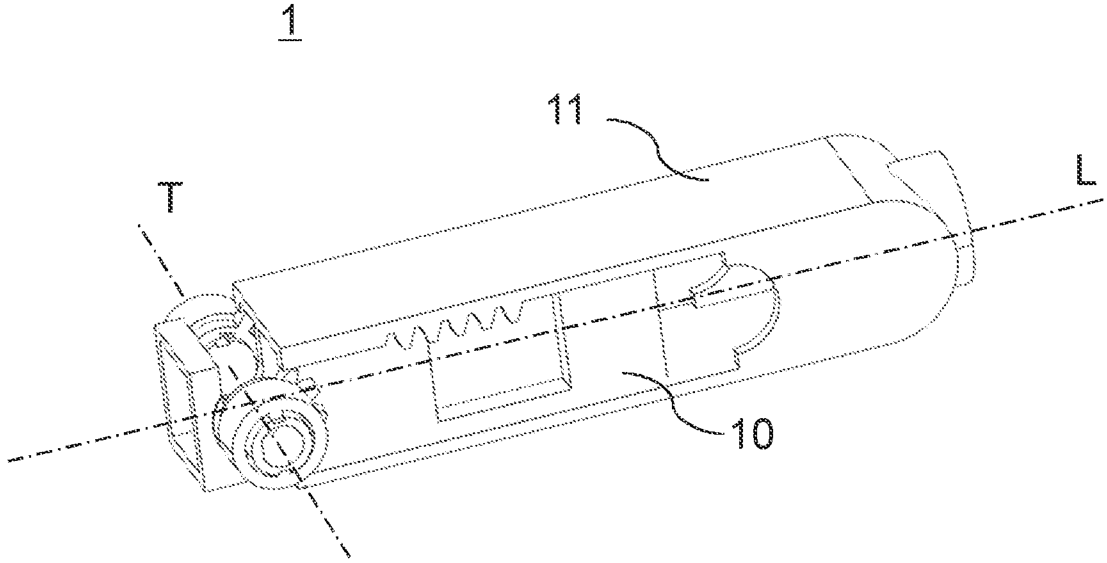
FIG. 1 schematically shows a perspective view of an assembly for a medicament delivery device.

The assembly 1 comprises an actuator 11 having a body 111 extending along the longitudinal axis L between a first end and a second end, as shown in FIG. 1. The actuator 11 is adjacent to the container holder 10 and movable relative to the container holder 10 along the longitudinal axis L. The actuator is rotationally fixed to the container holder; in a preferred example, the actuator is only movable relative to the container holder 10 along the longitudinal axis L.

The actuator 11 comprises an activation surface 110 attached to the body 111 of the actuator 11. The activation surface 110 of the actuator is fixed to the body of the actuator 11.

In one example, the activation surface of the actuator is an inclined surface angled relative to the longitudinal axis. In another example, the activation surface of the actuator is a protrusion protruding from a surface of the body of the actuator. In another example, the activation surface of the actuator 11 is a rack 110. The activation surface of the actuator can be arranged at one end of the body of the actuator, or arranged between the first end and the second end of the body of the actuator. The activation surface of the actuator will be explained in more detail later.

The actuator 11 is configured to apply a force for initiating an operation of the assembly 1 and therefore initiating an operation of the medicament delivery device comprising the assembly 1. For example, the body of the actuator 11 can be accessible to a user, so that the user may grip on or touch the actuator and manually move the actuator along the longitudinal axis L relative to the container holder 10; or the actuator may connect with a spring or a motor that moves the actuator along the longitudinal axis L once the spring or the motor has been released or initiated by the user.

In one example, the body 111 of the actuator 11 comprises one or more arms; in a preferred embodiment, the actuator 11 comprises two arms 111*a*, 111*b*. In a preferred example, the activation surface is arranged on the arm. The arm is configured to distribute the force applied on the actuator 11 in the direction of the longitudinal axis L. For example, the arm may provide a large contact surface connecting to an energy source, e.g. a coil spring, a motor or a gas canister, so that a relatively large energy source (usually also with a relatively higher accumulated force) can be connected to the actuator; or being gripped or touched by a user's hand. Alternatively, the arm can allow a user to more easily grip and initiate the movement of the actuator. For example, the arm 111*a*, 111*b* may be formed as two symmetrically arranged arms, so that the user can clamp the actuator between two fingers and initiate the assembly 1 with one hand. In another example, the body 111 of the actuator 11 comprises a tubular portion; the activation surface is arranged on an inner surface of the tubular portion of the body 111 of the actuator 11.

In a preferred example, if the actuator 11 comprises more than one arm 111*a*, 111*b*, the actuator 11 may comprise a join 111*c* connected between the arms 111*a*, 111*b*.

The assembly 1 comprises one or more drive assemblies 12, 12', 12", depending on the design of the medicament delivery device. When the assembly 1 comprises more than one drive assemblies 12, 12', 12", generally all of the drive assemblies are similar to one other, so only one drive assembly will be explained in detail, and such explanation regarding the drive assembly applies to any other drive assemblies if the assembly 1 comprises more than one drive assembly.

The drive assembly 12 is attached to the body 101 of the container holder 10. The drive assembly may be configured to eject a medicament contained within a medicament container received within the interior chamber 102 of the container holder 10, or the drive assembly may be configured to clamp or fix the medicament container to the retaining portion 103 of the container holder 10.

The drive assembly 12 comprises a motion converter and a rod 120 extending along a transverse axis T transverse to the longitudinal axis L. Preferably, the rod 120 comprises a rod body 120*a* extending along the transverse axis T transverse to the longitudinal axis L. The motion converter of the drive assembly is configured to interact with the activation surface of the actuator 11 so that a movement of the actuator 11 in the direction of the longitudinal axis L relative to the container holder 10 will be converted into a movement of the rod 120 in the direction of the transverse axis T relative to the container holder 10 through the interaction between the activation surface and the motion converter. The rod 120 can therefore move into the interior chamber 102 of the container holder 10, or move out from the interior chamber 102 of the container holder 10 when the actuator moves relative to the container holder in the direction of the longitudinal axis L.

In a preferred example, the activation surface and the motion converter are configured to mechanically engage each other to perform the interaction between the activation surface and the motion converter.

The motion converter of the drive assembly is connected to the rod 120, for example, the motion converter of the drive assembly can be attached to the rod body, or can be an integral part of the rod body.

As mentioned above, the activation surface of the actuator can be an inclined surface, a protrusion or a rack; the motion converter of the drive assembly is therefore formed correspondingly as will be explained with the following examples.

For example, when the activation surface of the actuator is an inclined surface, the motion converter of the drive assembly can be an inclined surface or a protrusion transversely protruding relative to the longitudinal axis from the body 101 of the container holder 10.

When the motion converter of the drive assembly is an inclined surface configured to contact with the inclined surface of the actuator, the inclined surface of the activation surface of the actuator is configured to face towards the inclined surface of the motion converter of the drive assembly. The inclined surface of the motion converter of the drive assembly is angled relative to the transverse axis T and the longitudinal axis; the inclined surface of the activation surface of the actuator is angled relative to the transverse axis T and the longitudinal axis L. Therefore, once the inclined surface of the motion converter of the drive assembly contacts with the inclined surface of the activation surface of the actuator, a movement of the actuator in the direction of the longitudinal axis L will push the motion converter of the drive assembly to move in the direction of the transverse axis T. The motion converter of the drive assembly is connected to the rod 120; so that a movement of the motion converter of the drive assembly in the direction of the transverse axis T causes the rod 120 to move along the transverse axis T.

Similarly, when the motion converter of the drive assembly is a protrusion, the protrusion is configured to contact with the inclined surface of the activation surface of the actuator. Once the protrusion of the motion converter of the drive assembly contacts the inclined surface of the activation surface of the actuator, a movement of the actuator in the direction of the longitudinal axis L will push the motion converter of the drive assembly to move in the direction of the transverse axis T. The motion converter of the drive assembly is connected to the rod 120; so that a movement of the motion converter of the drive assembly in the direction of the transverse axis T causes the rod 120 to move along the transverse axis T.

In another example, when the activation surface of the actuator is a protrusion, the motion converter of the drive assembly may comprise an inclined surface or a rotator. When the activation surface of the actuator is a protrusion and the motion converter of the drive assembly comprises an inclined surface, the inclined surface of the motion converter of the drive assembly is angled relative to the transverse axis T and the longitudinal axis L. The inclined surface of the drive assembly is configured to contact with the protrusion of the activation surface of the actuator. Once the protrusion of the activation surface of the actuator contacts with the inclined surface of the motion converter of the drive assembly, a movement of the actuator in the direction of the longitudinal axis L will push the motion converter of the drive assembly to move in the direction of the transverse axis T. The motion converter of the drive assembly is connected to the rod; so that a movement of the motion converter of the drive assembly in the direction of the transverse axis T causes the rod to move along the transverse axis T.

On the other hand, in an example where the activation surface of the actuator comprises a protrusion and the motion converter of the drive assembly comprises a rotator, the rotator is configured to be rotatable around the transverse axis T relative to the body 101 of the container holder 10 and fixed to the body 101 of the container holder 10 in the direction of the transverse axis T. In this example, the rotator comprises a body and a guide track on a surface of the body. For example, the guide track can be arranged on an outer surface of the body of the rotator. The protrusion of the activation surface of the actuator is configured to be positioned within or move into the guide track. The guide track can be formed by a ledge, a cut-out or a recess. When the protrusion of the activation surface of the actuator is in the guide track, the protrusion must follow the guide track. A movement of the actuator in the direction of the longitudinal axis L relative to the container holder 10 therefore causes the protrusion to rotate the rotator around the transverse axis T relative to the container holder.

The rotation of the rotator is configured to move the rod along the transverse axis T relative to the container holder, which arrangement will be explained in detail later.

In another example, the activation surface of the actuator is a rack 110, the motion converter of the drive assembly 12 can also be the rotator 121. In this example, the rotator 121 comprises teeth 121*b* extending outwardly relative to the transverse axis T from the outer surface of the body 121*a* of the rotator 121. The teeth 121*b* of the rotator 121 can be evenly distributed around the outer surface of the body 121*a* of the rotator 121; or only be distributed on a part of the outer surface of the body 121*a* of the rotator 121, as shown in FIGS. 3-4.

In examples where the motion converter of the drive assembly comprises the rotator, the rod 120 comprises a first engaging member 120*b* and a second engaging member 120*c*. The rotator comprises an engaging member 121*c* on a surface of the body 121*a* of the rotator 121. The first engaging member 120*b* of the rod 120 is configured to engage with the engaging member 121*c* of the rotator 121 thereby defining a first interface. The second engaging member 120*c* of the rod 120 is configured to engage with a counter engaging member of the body 101 of the container holder 10 thereby defining a second interface. One of the first interface and the second interface is a helical interface;

and the other one of the first interface and the second interface is a spline interface so that when the rotator 121 rotates relative to the container holder around the transverse axis T, the rod will be moved along the transverse axis T relative to the container holder.

Figure 3:
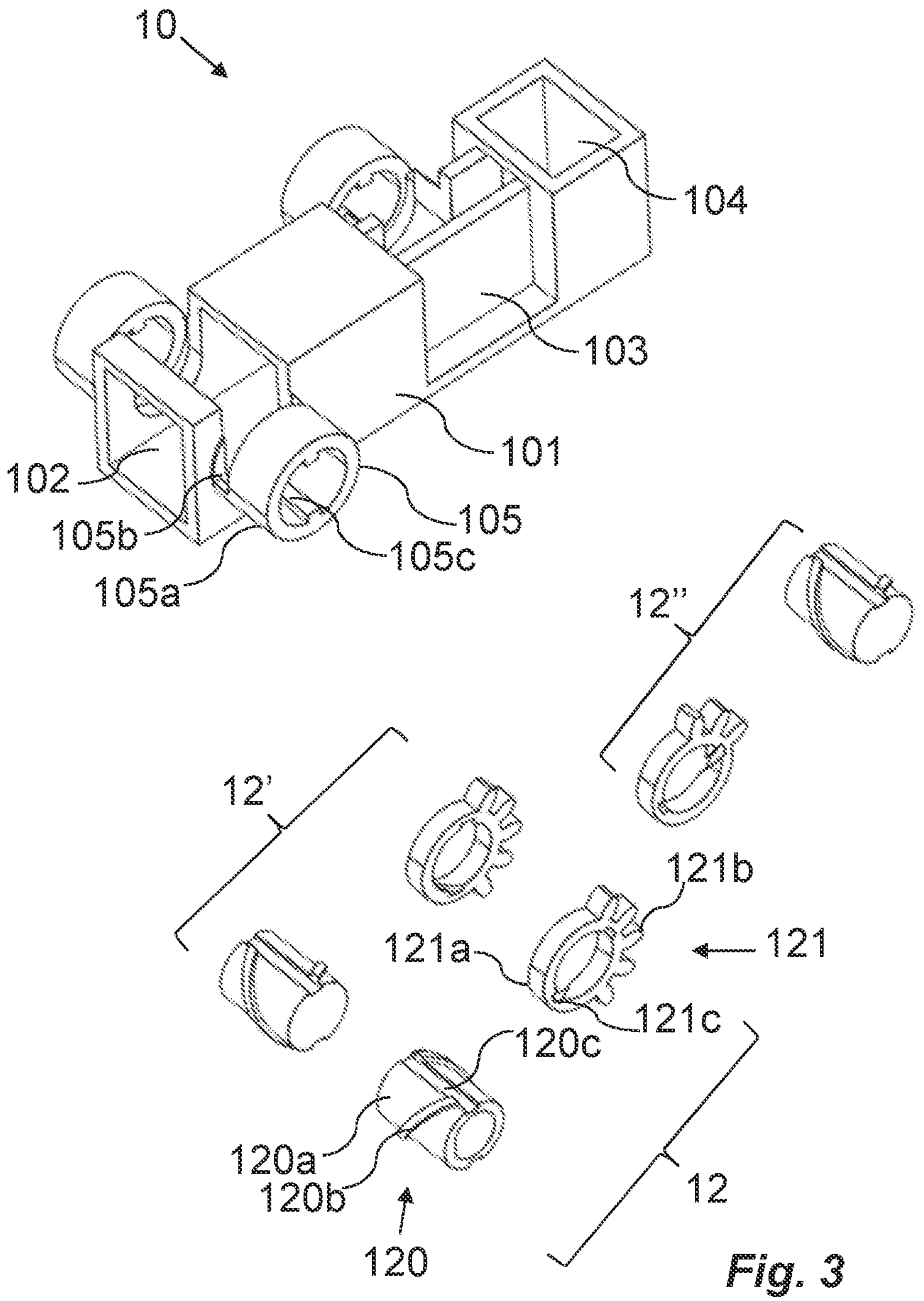
FIG. 3 schematically shows a perspective view of a container holder and a drive assembly of the assembly of FIG. 1.
Figure 4:
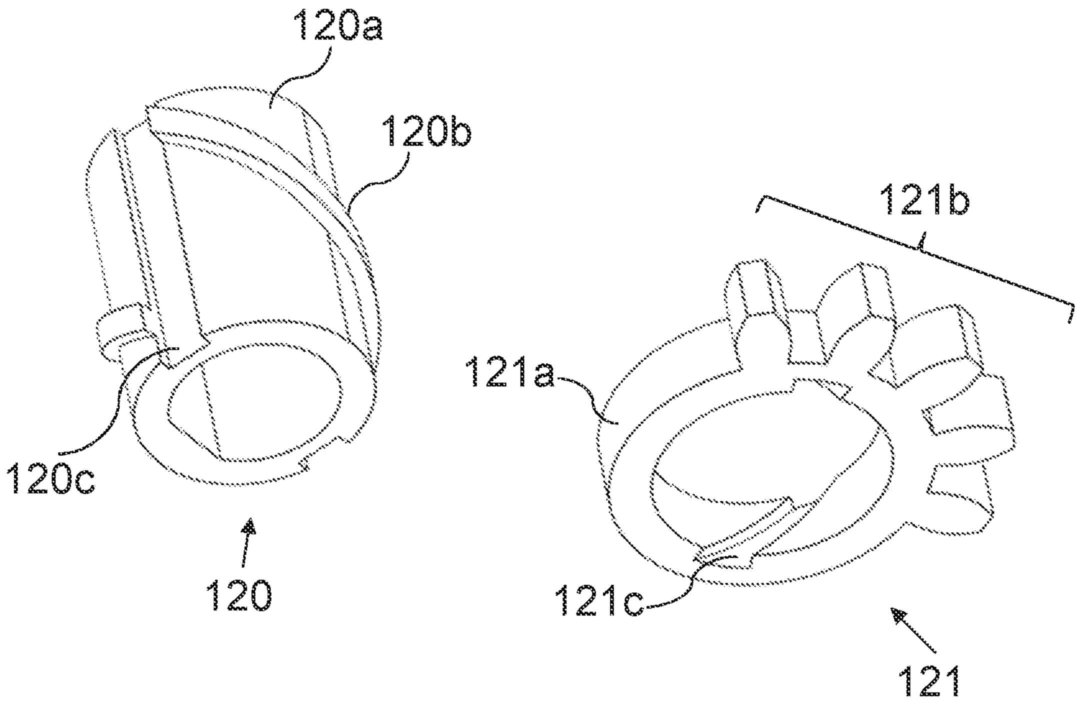
FIG. 4 schematically shows a perspective view of the drive assembly of FIG. 3.

In one example as shown in FIG. 3, the container holder 10 comprises a driving seat 105 for receiving the drive assembly 12. The driving seat 105 comprises a tubular body 105*a*, a cut-out 105*b*, and the counter engaging member 105*c* on the inner surface of the tubular body 105*a*. In one example, the tubular body 105*a* extends along the transverse axis T and the cut-out 105*b* extends circumferentially on the tubular body 150*a*. In the presented example, the body 121*a* of the rotator 121 is ring-shaped or tubular, and the engaging member 121*c* of the rotator 121 is arranged on an inner surface of the body 121*a* of the rotator 121. In this example, the rod 120 is arranged within the tubular body 105*a* of the driving seat 105, and the rotator 121 is arranged within the cut-out 105*b* of the driving seat 105.

Alternatively, the container holder 10 can be arranged without the driving seat 105. In this example, the body of the container holder may comprise one or more openings, dependent on the numbers of the drive assemblies. The one or more openings open in the direction of the transverse axis T. The rotator of the drive assembly can be attached on the inner or outer surface of the body of the container holder; the rod of the drive assembly is configured to move through the one or more openings of the body of the container holder. In this example, the counter engaging member 105*c* can be arranged on an inner surface of the one or more openings.

In another example, the container holder comprises two drive assemblies 12', 12" aligned parallel to one another on the body 101 of the container holder 10. The movement of the actuator 11 relative to the container holder 10 in the direction of the longitudinal axis L moves sequentially each rod of the two drive assemblies in the direction of the transverse axis T through the engagements between the two motion converters of the two drive assemblies and the activation surface of the actuator 11.

For example, the rack 110 of the activation surface of the actuator 11 aligns with teeth of the rotators of two drive assemblies 12', 12" in the direction of the longitudinal axis L. In this example, one of the two drive assemblies 12', 12" is configured to clamp or fix the medicament container to the interior chamber 102 of the container holder 10; and the other one of the two drive assemblies 12', 12" is configured to eject the contained medicament within the medicament container.

Alternatively, both drive assemblies 12', 12" are configured to eject the contained medicament within the medicament container. In another example, the container holder 10 comprises two drive assemblies 12, 12' aligned with one another along the transverse axis T on the body 101 of the container holder 10.

The actuator 11 comprises two activation surfaces; the movement of the actuator 11 relative to the container holder 10 in the direction of the longitudinal axis moves each rod of the two drive assemblies 12, 12' in the direction of the transverse axis T through the engagement between one motion converter of the two drive assemblies and one activation surface of the actuator 11 and the engagement between the other motion converter of the two drive assemblies and the other activation surface of the actuator 11.

For example, the two activation surfaces of the actuator 11 each comprise a rack. The two racks in the shown example are arranged between the first end of the body of the actuator 11 and the second end of the actuator 11; each tooth of the two racks extend in a direction perpendicular to the longitudinal axis and align respectively with teeth of rotators of the two drive assemblies 12, 12' in the direction of the longitudinal axis L. In this example, both drive assemblies 12, 12' are configured to eject the contained medicament within the medicament container.

Figure 5A:
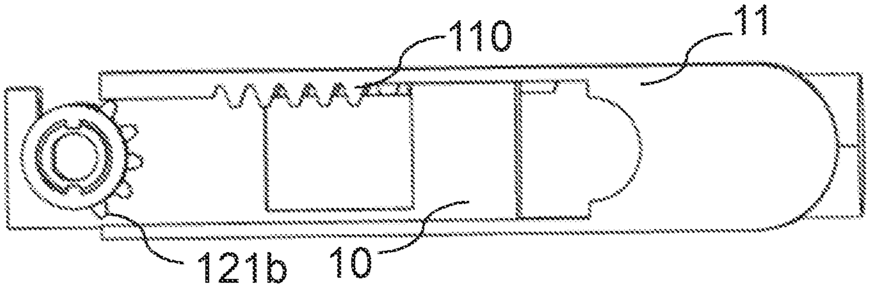
FIGS. 5A-5B schematically show side views of the assembly of FIG. 1.
Figure 5B:
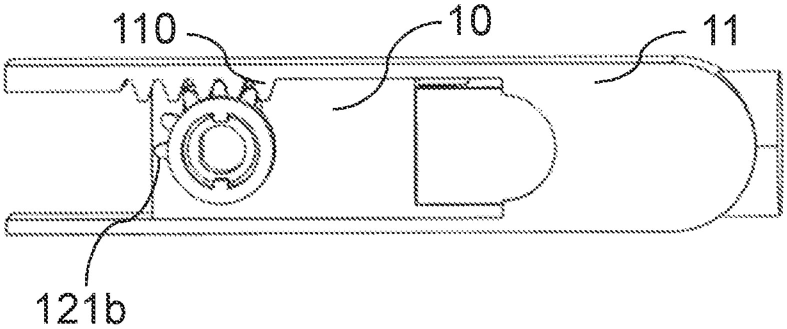

The teeth 121*b* of the rotator 121 is configured to mesh with the rack 110 of the activation surface of the actuator 11. The teeth 121*b* of the rotator 121 are aligned with the rack 110 of the activation surface of the actuator 11 in the direction of the longitudinal axis L. In a preferred example, the rotator 121 is axially fixed to the body 101 of the container holder 10 in the direction of the transverse axis T and the longitudinal axis L. When the actuator 11 is moved relative to the container holder 10 along the longitudinal axis L, the rack 110 of the activation surface of the actuator 11 meshes with the teeth 121*b* of the rotator 121. The rotator 121 is fixed to the body 101 of the container holder 10 in the direction of the longitudinal axis L, so that the axial movement of the actuator 11 along the longitudinal axis L rotates the rotator 121 around the transverse axis T, due to the mesh between the teeth 121*b* of the rotator 121 and the rack 110 of the activation surface of the actuator 11, as shown in FIGS. 5A-5B.

It should be noted that, alternatively, the rotator may be movable relative to the body of the container holder in the direction of the longitudinal axis L. For example, the drive assembly may be movable relative to the container holder in the direction of the longitudinal axis L. In this example, the rotator is movable also relative to the actuator 11. Therefore, the relative axial movement along the longitudinal axis between the rotator and the actuator rotates the rotator around the transverse axis T, due to the mesh between the teeth 121*b* of the rotator 121 and the rack 110 of the activation surface of the actuator 11.

Figure 6A:
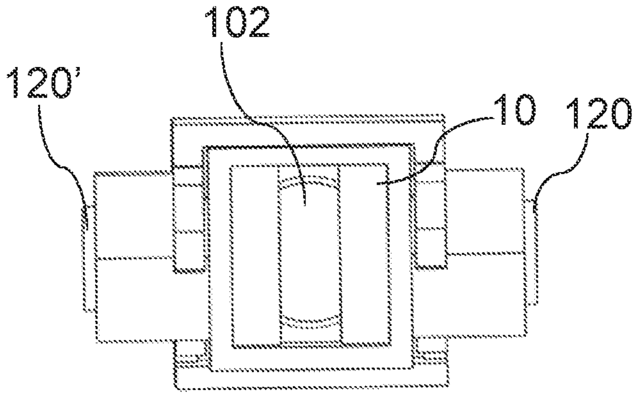
FIGS. 6A-6B schematically show front views of the assembly of FIG. 1 in the positions of FIGS. 5A-5B.
Figure 6B:
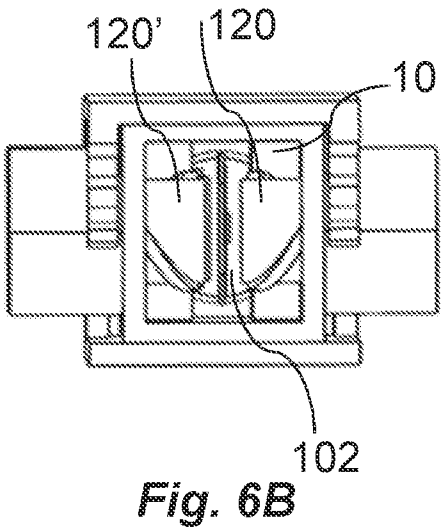

The rotation of the rotator 121 around the transverse axis T is configured to move the rod 120 in the direction of the transverse axis T relative to the body 101 of the container holder 10. This movement of the rod 120 that is initiated by the rotation of the rotator 121 is caused by an arrangement in which one of the first interface and the second interface is a helical interface; the other one of the first interface and the second interface is a spline interface as mentioned above. In the example, as shown in FIG. 3, the first interface is a helical interface. In this example, the first engaging member 120*b* of the rod 120 is a helical thread or a protrusion. The engaging member 121*c* of the rotator 121 is a helical thread when the first engaging member 120*b* of the rod 120 is a protrusion, or a protrusion when the first engaging member 120*b* of the rod 120 is a helical thread. In the example shown in FIG. 3, the first engaging member 120*b* of the rod 120 is the helical thread; and the engaging member 121*c* of the rotator 121 is the protrusion. Similarly, the second interface is a spline interface, namely, the second engaging member 120*c* of the rod 120 is a slot or a rib; and the counter engaging member 105*c* arranged on the body 101 of the container holder 10 is a slot when the second engaging member 120*c* of the rod 120 is a rib; or a rib when second engaging member 120*c* of the rod 120 is a slot or a rib. In the example shown in FIG. 3, the second engaging member 120*c* of the rod 120 is the slot; and the counter engaging member 105*c* arranged on the body 101 of the container holder 10 is the rib. As shown in FIGS. 6A-6B, when the actuator 11 moves relative to the body 101 of the container holder 10 along the longitudinal axis L in one direction, the rotator 121 rotates around the transverse axis T; such rotation is transferred into the axial movement of the rod 120 in the direction of the transverse axis T. In the presented example, the rod 120 therefore moving into the interior chamber 102, as shown in FIG. 6B.

When the drive assembly 12 is used to clamp or fix the medicament container to the interior chamber 102 of the container holder 10 together with retaining portion 103, the rod 120 can be transversely aligned with a ridge portion of the medicament container, or a portion of the medicament container that is not enclosing the contained medicament. When the rod 120 moves into the interior chamber 102 of the container holder 10, the rod 120 can therefore clamp the medicament container between the rod 120 and the inner surface of the retaining portion 103.

In the example that the drive assembly 12 is used to eject a medicament from a collapsible medicament container received within the interior chamber 102 of the container holder 10, the rod 120 is configured to act on the collapsible medicament container within the interior chamber 102 of the container holder 10. The rod 120 therefore, can squeeze the medicament contained within the collapsible medicament container out between the rod 120 and the inner surface of the body 101 of the container holder 10 or between two rods 120, 120' as shown in FIG. 6B in the example that the assembly 1 comprises a two or more drive assemblies.

The assembly may be designed as a disposable assembly or a reusable assembly. When the assembly is disposable, the activation surface of the actuator is configured to fully disconnected with the motion converter of the drive assembly. For example, the rack of the activation surface of the actuator can be fully disengaged and misaligned with the teeth of the rotator of the motion converter of the drive assembly when the actuator moves along the longitudinal axis L relative to the container holder with a predetermined distance. Once the actuator axially moves along the longitudinal axis L relative to the container holder with the predetermined distance, any further movement of the actuator relative to the container holder along the longitudinal axis L cannot be transferred to the drive assembly.

Alternatively, when the assembly 1 is reusable, the activation surface of the actuator is configured to connect with the motion converter of the drive assembly all the time. Therefore, the movement of the actuator 11 relative to the container holder 10 along the longitudinal axis L in one direction may cause the rod 120 moves into the interior chamber 102 of the container holder 10. Therefore, the rod 120 can clamp or squeeze the contained medicament container. Any further or reverse movement of the actuator 11 relative to the container holder 10 along the longitudinal axis L may cause the rod 120 to move out from the interior chamber 102 of the container holder 10. As a result, the rod 120 can disengage with the contained medicament container.

In a preferred example, the assembly 1 is reusable. In another preferred example, the assembly 1 comprises three drive assemblies 12, 12', 12", as shown in FIG. 3. One of the three drive assemblies 12, 12', 12" is configured to clamp a portion of a collapsible medicament container, and the other two of the three drive assemblies 12, 12', 12" are configured to eject the medicament contained within the medicament container. Preferably, the two of the three drive assemblies 12, 12', 12" for ejecting the medicament contained within the medicament container are symmetrically arranged on two sides of the body 101 of the container holder 10; the rod of each drive assembly 12, 12', 12" is facing towards other rods along the transverse axis T. In a preferred example, when the assemblies are designed to eject the medicament by two drive assemblies 12, 12', the rods of the two drive assemblies are coaxial to each other in the direction of the transverse axis T.

Figure 7:
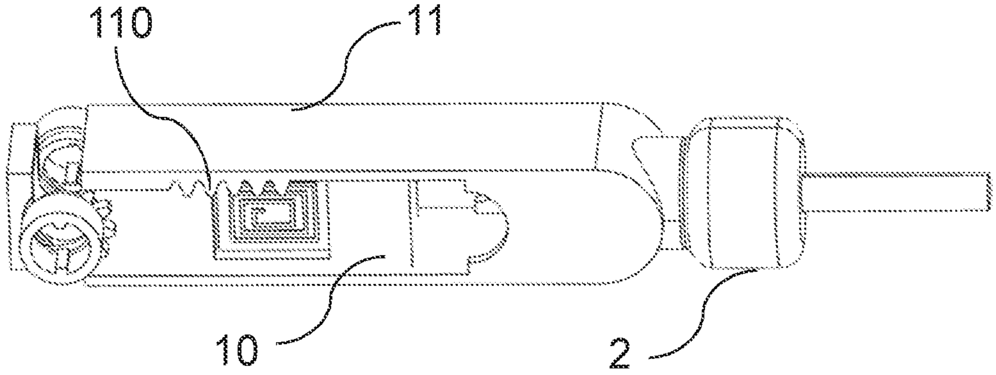
FIG. 7 schematically shows a perspective view of the assembly of FIG. 1 with a motor.
Figure 8:
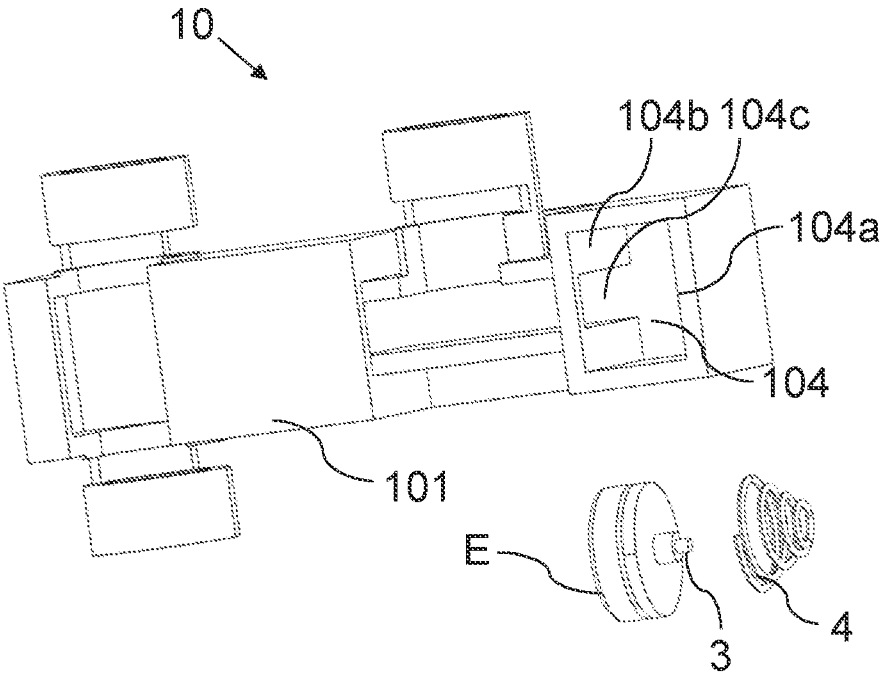
FIG. 8 schematically shows a perspective view of the container holder of FIG. 3 with an electronics set and a biasing member.

The assembly 1 may comprise a motor 2, e.g. step motor, connected to the actuator 11, as shown in FIG. 7. In another example, the assembly 1 may comprise a switch 3 connected with an electronics set E, as shown in FIG. 8. The electronics set E may comprise any one of a processor, a wireless communication receiver/transmitter, a vibration motor, a buzzer, a memory, an NFC/RFID circuit, a sensor, a timer, or any combination thereof.

In one example, the switch 3 and the electronics set E are arranged within the distal partition 104 of the container holder 10. The switch 3 is movable relative to the electronics set E and/or the body 101 of the container holder 10 between an open position and a closed position. When the switch 3 is moved into the closed position, the assembly 1 may be designed that the motor 2 will therefore be activated and initiate the movement of the actuator 11 relative to the body 101 of the container holder 10; alternatively, an operation from the electronics set E may be triggered.

The switch may be pivotable relative to the electronics set E and/or the body of the container holder between the open position and the closed position. Alternatively, the switch 3 is linearly movable relative to the electronics set E and/or the body of the container holder between the open position and the closed position along a linear path, in a direction of the longitudinal axis L, or in a direction perpendicular to the longitudinal axis L.

The switch may be accessible to the user; that is, the user may directly contact and manually move the switch between the open position and the closed position. Alternatively, the switch may be inaccessible to the user; that is, the user cannot directly contact or move the switch between the open position and the closed position and instead the switch is moved by a component of the medicament delivery device comprising the assembly 1.

For example, the switch 3 may be moved by the medicament container received within the interior chamber 102 of the container holder 10. In this example, the distal partition 104 may be formed by a distal wall 104*a* and a ledge 104*b*. The electronics set E and the switch 3 are received between the distal wall 104*a* and the ledge 104*b*. In a preferred example, the switch 3 is attached to the electronics set E, as shown in FIG. 8. The ledge 104*b* of the distal partition comprises a cut-out 104*c*. A shape of the cut-out is dependent on the shape of at least a portion of the medicament container, and a direction for loading the medicament container into the interior chamber 102 of the container holder 10. For example, the medicament container may be loaded into the interior chamber 102 of the container holder 10 by moving along the longitudinal axis L from the proximal end of the container holder 10. In this example, the cut-out 104*c* is in a direction of longitudinal axis L; the cut-out 104*c* is formed as a corresponding shape to a distal portion of the medicament container so that the distal portion of the medicament container can pass through the cut-out 104*c*. In this example, upon loading the medicament container, the distal portion of the medicament container moves past the cut-out 104*c*, and presses on the electronics set E in the distal direction. When the distal portion of the medicament container presses on the electronics set E, the switch 3 is moved toward the distal wall 104*a* of the distal partition 104. When the switch 3 contacts the distal wall 104*a*, a reaction force between the distal wall 104*a* of the distal partition 104 moves the switch 3 from the open position to the closed position.

In another example, the assembly 1 optionally comprises a biasing member 4; in one example, the biasing member 4 can be a compression coil spring. Preferably, the biasing member 4 can be used when the switch 3 is linearly movable relative to the electronics set E and/or the body 101 of the container holder 10. The biasing member 4 is compressible between a relaxed position and a compressed position along the linear path of the switch 3. The biasing member 4 at least partially surrounds the switch 3; a linear moving distance between the relaxed position of the biasing member 4 and the compressed position of the biasing member 4 is longer than a linear moving distance between the open position of the switch and the closed position of the switch 3. The switch 3, therefore, cannot be moved into the closed position from the open position without first moving the biasing member 4 into the compressed position.

The biasing member 4, therefore, can be a security mechanism to avoid unintentionally initiating the actuator 11 or any other unintentional operation of the electronics set E due to any accidental contact with the switch 3.

Further, some of the medicament containers comprise a preassembled delivery member, e.g. a needle, attached to the medicament container without a fluid connection with the contained medicament before use. Some of those medicament containers require the user to establish the fluid connection between the delivery member and the contained medicament, for example by pushing the medicament delivery member towards the contained medicament. When the assembly 1 is used with those medicament containers, the user needs to push the delivery member to establish the fluid connection between the delivery member and the contained medicament. The biasing member 4 can therefore be another type of security mechanism to make sure the user has properly established the fluid connection between the delivery member and the contained medicament before using the assembly 1 for delivering the contained medicament. In this example, the linear moving path of the switch 3 is aligned with a moving path of the delivery member, namely the moving path that the user linearly moves the delivery member to establish the fluid connection between the delivery member and the contained medicament. Further, the biasing member 4 may be chosen with a force greater than a force needed to establish the fluid connection between the delivery member and the contained medicament. For example, the delivery member may be snapped onto the medicament container for establishing the fluid connection between the delivery member and the contained medicament by at least 4N pushing force; in this example, the assembly 1 may comprise the biasing member 4 with a certain elastic potential energy so that the biasing member 4 can be moved into the compressed position by at least 5N force.

Figure 9:
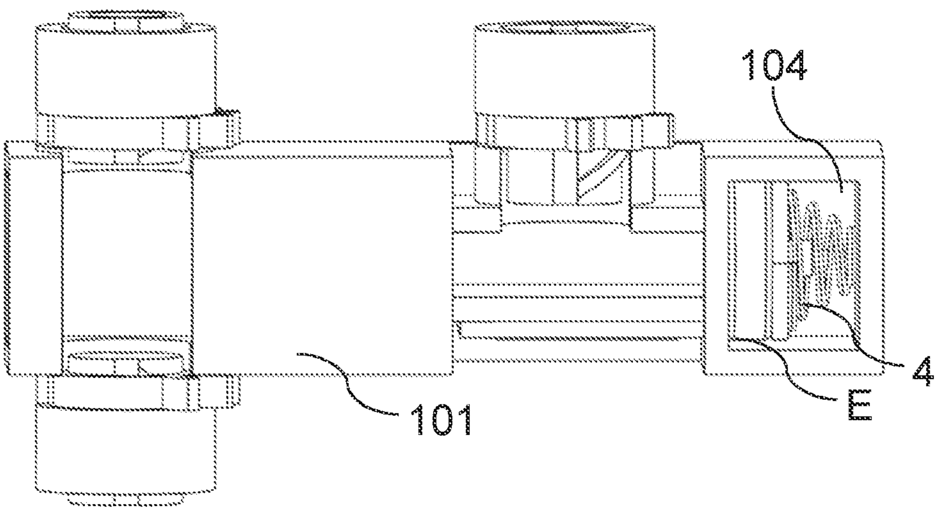
FIG. 9 schematically shows a top view of the container holder of FIG. 8 with the electronics set and the biasing member of FIG. 8.
Figure 11:
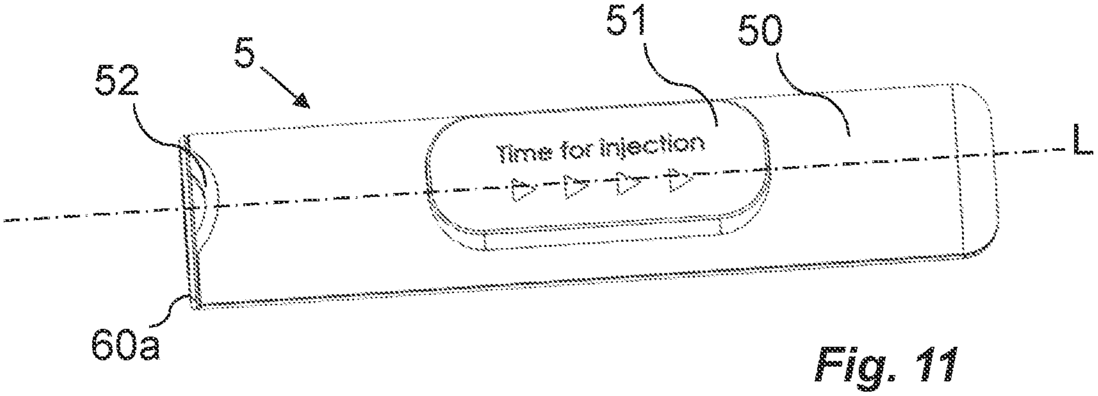
FIG. 11 schematically shows a perspective view of a medicament delivery device.

In one example, the assembly 1 is configured to have a medicament container loaded into the interior chamber 102 of the container holder 10 by inserting the medicament container from the proximal end of the container holder 10. The body 101 of the container holder 10 is dimensioned to fully cover the medicament container except for a front cap (usually for covering the preassembled delivery member). Alternatively, if the assembly 1 is used with a medicament delivery device with an outer shell (as shown in FIG. 11), then the body 101 of the container holder 10 doesn't need to fully cover the medicament container. The user will be instructed to push on the preassembled delivery member through the front cap to load the medicament container into the interior chamber 102 of the container holder 10. The switch 3, the biasing member 4 and the electronics set E are all arranged between the distal wall 104*a* and the ledge 104*b* of the distal partition 104. In a preferred example, the biasing member 4 member is a compression coil spring; and the switch is surrounded by the compression coil spring 4, as shown in FIG. 9. In this presented example, the biasing member 4 is positioned along the longitudinal axis L between the electronics set E and the distal wall 104*a* of the distal partition 104.

Figure 10:
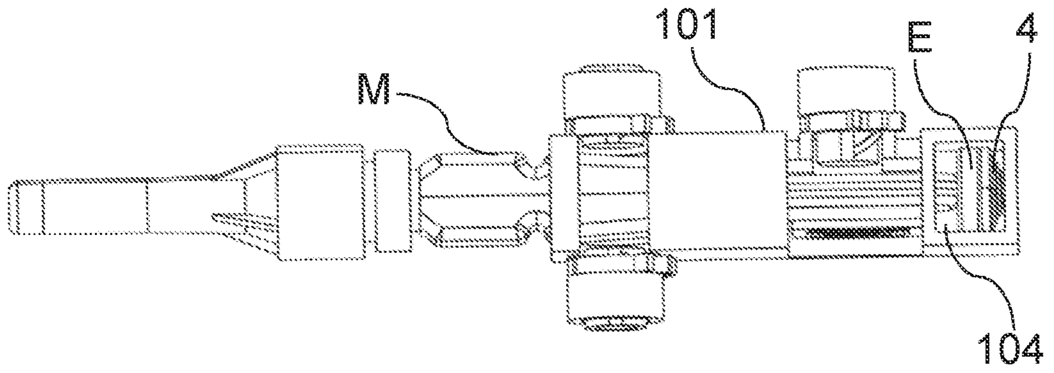
FIG. 10 schematically shows a top view of the container holder of FIG. 9 with a medicament container.

When the user loads a medicament container M into the body 101 of the container holder 10 by pushing on the front cap of the medicament container M towards the distal end of the container holder 10 along the longitudinal axis L, as shown in FIG. 10, the distal portion of the medicament container M protrudes into the distal partition 104 and pushes on the electronics set E. When the pushing force applied on the medicament container M is great enough to move the biasing member 4 from the relaxed position to the compressed position, meaning the force is also great enough to establish the fluid connection between the delivery member and the contained medicament, the switch 3 can be moved into the closed position by the reaction force between the distal wall 104*a* and the switch 3.

Figure 13:
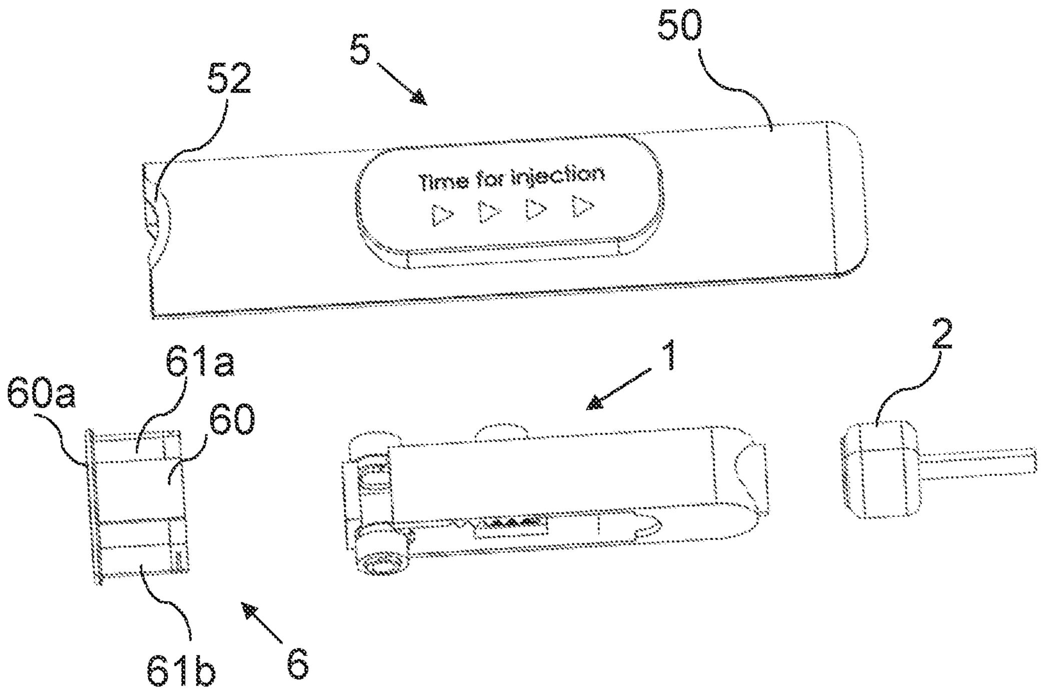
FIG. 13 schematically shows a perspective view of components of the medicament delivery device of FIG. 11.

FIG. 11 illustrates a medicament delivery device 5 comprising the assembly 1. In this presented example, the medicament delivery device 5 comprises the outer shell 50 extending along the longitudinal axis L between a proximal end and a distal end. The outer shell 50 is configured to accommodate the container holder 10. In one example, the container holder 10, the actuator 11 and a power source, e.g. a motor or a spring, are all fully arranged within the outer shell 50, as shown in FIG. 13. In another example, the container holder is arranged within the outer shell; and the actuator is partially arranged within the outer shell 50, so that the user can manually move the actuator relative to the outer shell 50 along the longitudinal axis L. The container holder can be fixed to the outer shell, or axially movable in the direction of the longitudinal axis L relative to the outer shell.

The medicament delivery device 5 may comprise a user interface 51 providing indications/instructions to the user, through one or more texture, mark, light, sound and/or vibration. The user interface 51 can be an LCD display or E-Ink, for example; the user interface 51 may connect with the electronics set E, the switch 3 and/or the motor 2 of the assembly. The user interface 51 may be a touch panel with which the user can input data or trigger one or more operations of the medicament delivery device 5. For example, the user interface 51 may be configured to be activated by moving the switch 3 into the closed position, and the motor may be configured to be controlled by the user input from the user interface 51. Alternatively, the user interface 51 can be a transparent window aligned with the medicament container for the user to observe the contained medicament.

Figure 12:
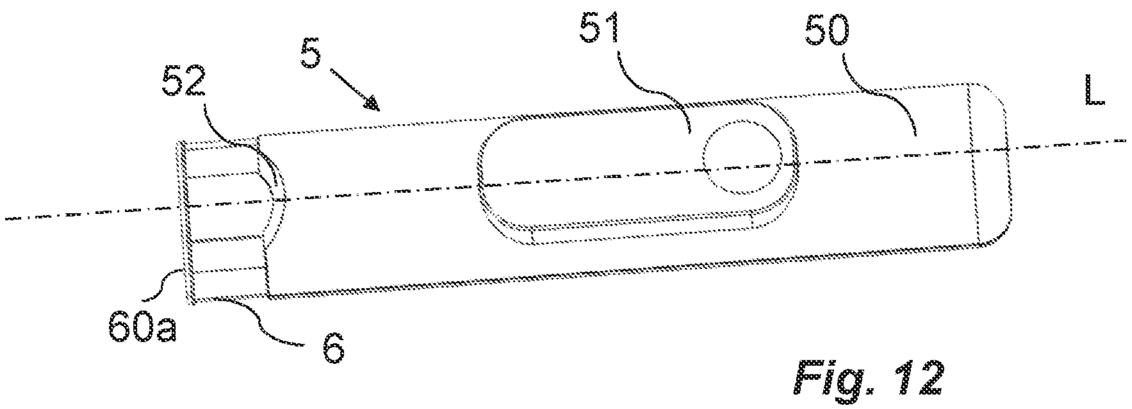
FIG. 12 schematically shows a perspective view of the medicament delivery device of FIG. 11.

In another example, the medicament delivery device 5 comprises a delivery member guard 6, as shown in FIG. 12. The delivery member guard 6 comprises a tubular body 60 with a contact portion 60*a* for contacting the medicament delivery site and a central passage 60*b* for accommodating the medicament delivery member connected to the medicament container. The delivery member guard 6 is attached to the outer shell 50 and axially movable relative to the outer shell 50 in the direction of the longitudinal axis L between an extended position, as shown in FIG. 12, and a retracted position, as shown in FIG. 11.

In one example, the delivery member guard is optionally connected to a guard biasing member. The guard biasing member can be a spring or a flexible arm arranged between an inner surface of the outer shell and the delivery member guard 6. In this example, the guard biasing member is configured to bias the delivery member guard to the extended position. In another example, the delivery member guard 6 is configured to be moved to the extended position from the retracted position by the user manually pulling on the contact portion 60*a* of the delivery member guard 6. In this example, the outer shell 50 of the medicament delivery device 5 comprises a concave portion 52 arranged on the proximal edge of the outer shell and facing towards the proximal end of the medicament delivery device 5. Therefore, the user can grip on the contact portion 60*a* through the concave portion 52 of the outer shell 50 for pulling the delivery member guard 6 to the extended position.

Figure 14A:
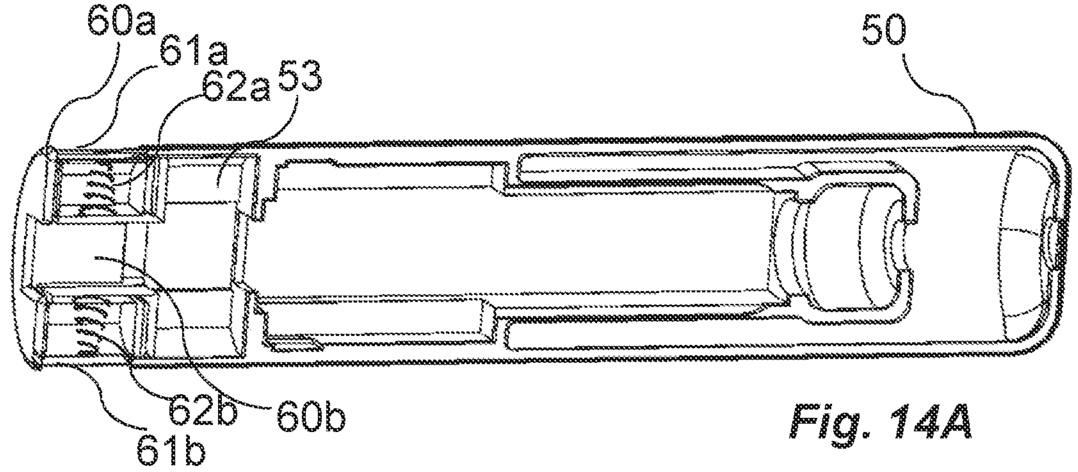
FIGS. 14A-14B schematically show side views of the medicament delivery device of FIG. 11.
Figure 14B:
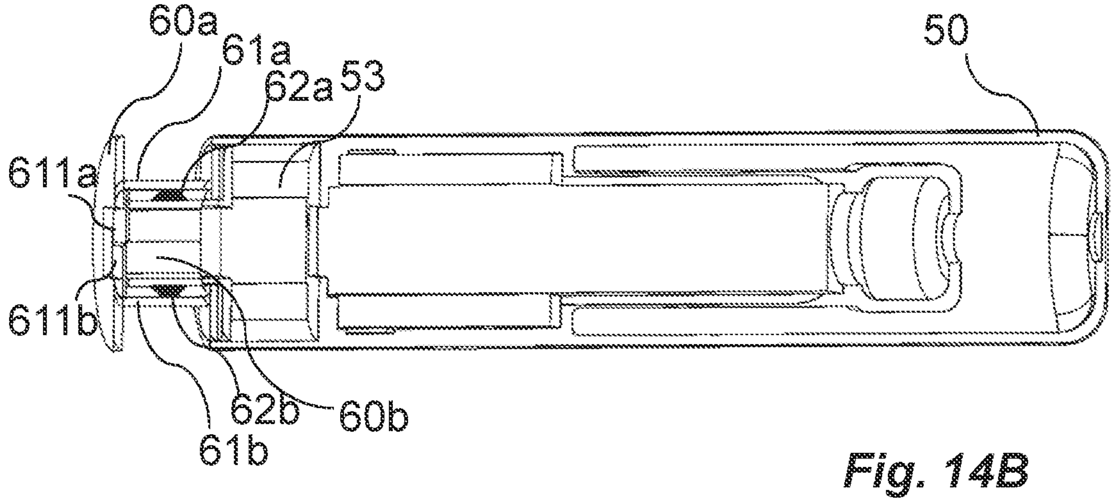

In the example presented in FIG. 13, the medicament delivery device 5 comprises the assembly 1 with the motor 2 for moving the actuator along the longitudinal axis L relative to the container holder 10. The delivery member guard 6 in the presented example comprises the tubular body 60 and two symmetrically arranged buttons 61*a*, 61*b* arranged on an outer surface of the guard body 60 and facing towards one another. The two buttons 61*a*, 61*b* are movable relative to the tubular body 60 and the outer shell in the direction of the transverse axis T. The two buttons 61*a*, 61*b* are movable relative to the tubular body 60 and the outer shell 50 between a relaxed position and a pressed position where the two buttons 61*a*, 61*b* are closer to each other in the direction of the transverse axis T than in the relaxed position, as shown in FIG. 14A-14B.

The delivery member guard 6 further comprises two biasing elements 62*a*, 62*b*. Preferably, the two biasing elements 62*a*, 62*b* are two compression coil springs. The two biasing elements 62*a*, 62*b* are arranged between inner surfaces of the two buttons 61*a*, 61*b* respectively and corresponding surfaces of the guard body 60. The two biasing elements 62*a*, 62*b* are configured to push the two buttons 61*a*, 61*b* respectively in the direction of the transverse axis T from the pressed position to the relaxed position.

In one example, each of the two buttons 61*a*, 61*b* comprises a blade 611*a*, 611*b* fixed to the button. Each blade 611*a*, 611*b* extends in the direction of the transverse axis T and faces to each other. When the two buttons move towards one another from the relaxed position to the pressed position, as shown in FIG. 14B, the two blades 611*a*, 611*b* are moved towards one another together with the two buttons. The two blades 611*a*, 611*b*, therefore, move further into the central passage 60*b* of the delivery member guard 6. When the user has completed the medicament delivery operation, the user may press the two buttons into the pressed position so that the blades 611*a*, 611*b* can cut the medicament delivery member received within the central passage 60*b* of the delivery member guard 6. The blades 611*a*, 611*b* may be configured to contact with each other, or overlap to each other in the longitudinal axis, or move close to each other without contact when the two buttons 61*a*, 61*b* are in the pressed position, dependent on a dimension of the medicament delivery member received within the central passage 60*b* of the delivery member guard 6.

Figure 15A:
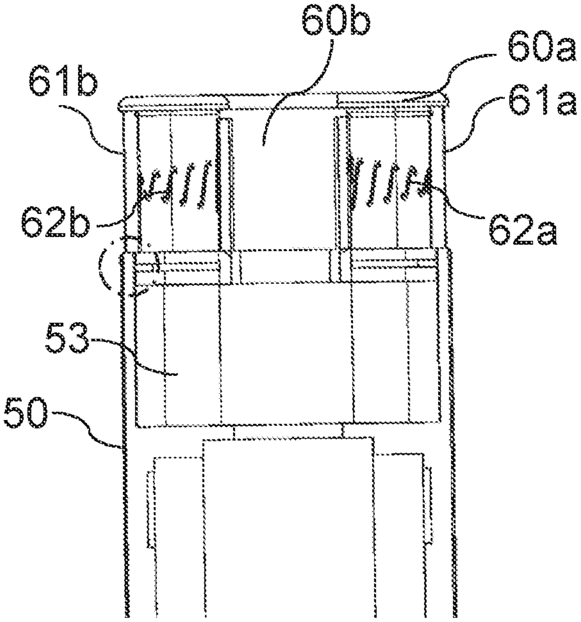
FIGS. 15A-15B schematically show side views of a proximal portion of the medicament delivery device of FIG. 11.
Figure 15B:
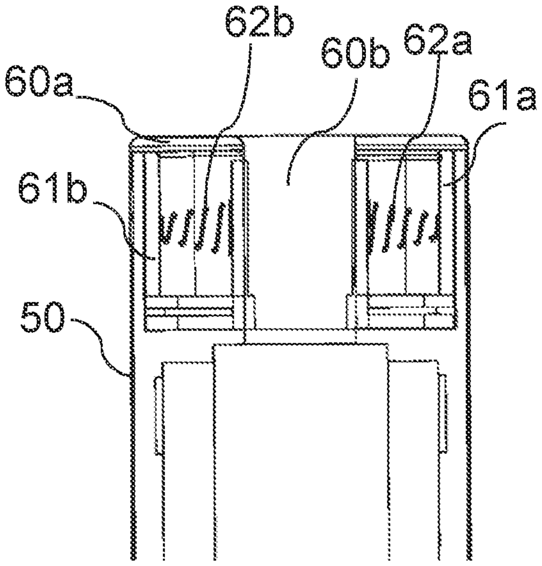

The outer shell 50 of the medicament delivery device 5 comprises an inner proximal portion 53 for receiving the two buttons 61*a*, 61*b* when the delivery member guard 6 is in the retracted position. In a preferred example, the two buttons 61*a*, 61*b* protrude transversely from the outer shell 50 (as highlighted by a dashed line in FIG. 15A) when the two buttons in the relaxed position. Therefore, when the two buttons 61*a*, 61*b* are received within the inner proximal portion 53 of the outer shell 50, the two buttons 61*a*, 61*b* will press on inner surfaces of the outer shell 50 due to the force from the two biasing elements 62*a*, 62*b*. The delivery member guard 6 is, therefore, press fitting to the outer shell 50 in the retracted position, as shown in FIG. 15B. When the user pulls the delivery member guard 6 to the extended position, the two buttons 61*a*, 61*b* move to the relaxed position. When the two buttons 61*a*, 61*b* are in the relaxed position, distal edges of the two buttons 61*a*, 61*b* abut the proximal edge of the outer shell, therefore, the delivery member guard 6 cannot move to the retracted position unless the two buttons 61*a*, 61*b* are pressed. A longitudinal length of the two buttons 61*a*, 61*b* can therefore determine a user-accessible portion of the delivery member. For example, when the delivery member is a needle, the user-accessible portion of the delivery member should be the portion that is not covered by the tubular body 60 of the delivery member guard 6. The user-accessible portion of the needle is usually equal to an injection depth (since the user-accessible portion of the needle can be fully inserted into an injection site), so the longitudinal length of the two buttons 61*a*, 61*b* can therefore be used to fix the injection depth.

The inventive concept has mainly been described above with reference to a few examples. However, as is readily appreciated by a person skilled in the art, other embodiments than the ones disclosed above are equally possible within the scope of the inventive concept, as defined by the appended claims.

Some aspects of the present disclosure are described in the clauses below.

1. An assembly for a medicament delivery device, the assembly comprising:
   - a container holder comprising a body extending along a longitudinal axis between a proximal and a distal end, the body defining an interior chamber for receiving a medicament container;
   - an actuator connected to the container holder and axially movable relative to the body of the container holder; and
   - a drive assembly attached to the body of the container holder;
   - wherein the drive assembly comprises a motion converter and a rod;
   - wherein the actuator comprises an activation surface movable relative to the motion converter of the drive assembly in the direction of the longitudinal axis; and wherein a movement of the actuator relative to the container holder in the direction of the longitudinal axis is converted to a movement of the rod relative to the container holder along a transverse axis transverse to the longitudinal axis through an engagement between the motion converter of the drive assembly and the activation surface of the actuator.

2. The assembly for a medicament delivery device according to clause 1, wherein the motion converter of the drive assembly is attached to the rod.

3. The assembly for a medicament delivery device according to clause 1 or 2, wherein the motion converter of the drive assembly comprises an inclined surface angled to the transverse axis and the longitudinal axis.

4. The assembly for a medicament delivery device according to any one of the preceding clauses, wherein the activation surface of the actuator comprises an inclined surface angled relative to the transverse axis and the longitudinal axis.

5. The assembly for a medicament delivery device according to the combination of clause 3 and clause 4, wherein the inclined surface of the motion converter of the drive assembly is configured to face towards the inclined surface of the activation surface of the actuator.

6. The assembly for a medicament delivery device according to clause 4, wherein the motion converter of the drive assembly comprises a protrusion extending from the body of the container holder in the direction of the transverse axis.

7. The assembly for a medicament delivery device according to any one of the preceding clauses, wherein the motion converter of the drive assembly comprises a rotator fixed to the body of the container holder in the direction of the transverse axis and rotatable around the transverse axis relative to the body of the container holder; and wherein the rotator comprises a body comprising an outer surface.

8. The assembly for a medicament delivery device according to clause 3 or 7, wherein the activation surface of the actuator comprises a protrusion.

9. The assembly for a medicament delivery device according to clause 8 when dependent on clause 3, wherein the protrusion of the activation surface of the actuator extends in the direction of the longitudinal axis.

10. The assembly for a medicament delivery device according to clause 8 when dependent on clause 7, wherein the rotator comprises a guide track on the outer surface of the body of the rotator; wherein the protrusion of the activation surface of the actuator extends in a direction perpendicular to the longitudinal axis; and wherein the protrusion of the activation surface of the actuator follows the track of the rotator when the actuator moves relative to the rotator in the direction of the longitudinal axis.

11. The assembly for a medicament delivery device according to clause 7, wherein the rotator comprises teeth extending outwardly relative to the transverse axis from the outer surface of the body of the rotator; wherein the activation surface of the actuator comprises a rack; wherein each tooth of the rack extends in a direction perpendicular to the longitudinal axis; and wherein the rack aligns with the teeth of the rotator in the direction of the longitudinal axis.

12. The assembly for a medicament delivery device according to any one of clauses 7 and 10-11, wherein the rotator comprises an engaging member on a surface of the body of the rotator; wherein the rod comprises a first engaging member engaged with the engaging member of the rotator thereby defining a first interface; wherein the rod comprises a second engaging member engaged with a counter engaging member of the body of the container holder thereby defining a second interface; and wherein one of the first interface and the second interface is a helical interface; and the other one of the first interface and the second interface is a spline interface.

13. The assembly for a medicament delivery device according to clause 12, wherein the first interface is a helical interface.

14. The assembly for a medicament delivery device according to clause 13, wherein the first engaging member of the rod is a helical thread; and wherein the engaging member of the rotator is a protrusion.

15. The assembly for a medicament delivery device according to clause 13, wherein the first engaging member of the rod is a protrusion; and wherein the engaging member of the rotator is a helical thread.

16. The assembly for a medicament delivery device according to clause 13 or 14, wherein the second engaging member of the rod is a rib.

17. The assembly for a medicament delivery device according to clause 13 or 14, wherein the second engaging member of the rod is a slot.

18. The assembly for a medicament delivery device according to clause 16 or 17, wherein the counter engaging member arranged on the body of the container holder is a rib.

19. The assembly for a medicament delivery device according to clause 16, wherein the counter engaging member arranged on the body of the container holder is a slot.

20. The assembly for a medicament delivery device according to clause 12, wherein the second interface is a helical engagement.

21. The assembly for a medicament delivery device according to clause 20, wherein the second engaging member of the rod is a helical thread; and wherein the counter engaging member of the body of the container holder is a protrusion.

22. The assembly for a medicament delivery device according to clause 20, wherein the second engaging member of the rod is a protrusion; and wherein the counter engaging member of the body of the container holder is a helical thread.

23. The assembly for a medicament delivery device according to clause 21 or 22, wherein the first engaging member of the rod is a rib.

24. The assembly for a medicament delivery device according to clause 21 or 22, wherein the first engaging member of the rod is a slot.

25. The assembly for a medicament delivery device according to clause 23 or 24, wherein the engaging member of the rotator is a rib.

26. The assembly for a medicament delivery device according to clause 23, wherein the engaging member of the rotator is a slot.

27 The assembly for a medicament delivery device according to any one of clause 7-8 and 10-21, wherein the body of the rotator is ring-shaped or tubular.

28. The assembly for a medicament delivery device according to clause 27, wherein the engaging member of the rotator is arranged on an inner surface of the body of the rotator.

29. The assembly for a medicament delivery device according to any one of preceding clauses, wherein the rod comprises a rod body extending along the transverse axis.

30. The assembly for a medicament delivery device according to clause 29, dependent on the combination of clause 28 and clause 12, wherein the body of the rotator at least partially encloses the rod body; and wherein the first engaging member of the rod is arranged on an outer surface of the rod body.

31. The assembly for a medicament delivery device according to any one of clauses 7-8 and 10-21, wherein the engaging member of the rotator is arranged on the outer surface of the body of the rotator.

32. The assembly for a medicament delivery device according to clause 29 when dependent on the combination of clause 25 and clause 12, wherein the rod body comprises a tubular portion at least partially enclosing the body of the rotator; and wherein the first engaging member of the rod is arranged on an inner surface of the tubular portion of the rod body.

33. The assembly for a medicament delivery device according to clause 29, wherein the second engaging member of the rod is arranged on an outer surface of the rod body.

34. The assembly for a medicament delivery device according to any one of clause 12-28 when dependent on clause 29, wherein the rod body comprises a tubular portion;

and wherein the second engaging member of the rod is arranged on an inner surface of the tubular portion of the rod body.

35. The assembly for a medicament delivery device according to any one of the preceding clauses, the assembly comprising: two drive assemblies aligned parallel to one another on the body of the container holder; wherein the movement of the actuator relative to the container holder in the direction of the longitudinal axis is configured to move sequentially each rod of the two drive assemblies along the transverse axis through the engagements between the two motion converters of the two drive assemblies and the activation surface of the actuator.

36. The assembly for a medicament delivery device according to any one of the preceding clauses, the assembly comprising: two drive assemblies aligned coaxially to one another in the direction of the transverse axis on the body of the container holder; wherein the actuator comprises two activation surfaces; wherein the movement of the actuator relative to the container holder in the direction of the longitudinal axis moves each rod of the two drive assemblies in the direction of the transverse axis through the engagement between one motion converter of the two drive assemblies and one activation surface of the actuator; and the engagement between the other one motion converter of the two drive assemblies and the other one activation surface of the actuator.

37. The assembly for a medicament delivery device according to any one of clauses 7 and 10-36, wherein the rotator is fixed to the body of the container holder in the direction of the longitudinal axis.

38. The assembly for a medicament delivery device according to any one of the preceding clauses, the assembly comprising: a motor connected to the actuator and a switch attached to the container holder; wherein the switch is movable relative to the body of the container holder between an open position and a closed position where the motor is configured to initiate the movement of the actuator relative to the body of the container holder.

39. The assembly for a medicament delivery device according to clause 37, wherein the switch is movable relative to the body of the container holder between the open position and the closed position along a linear path.

40. The assembly for a medicament delivery device according to clause 38, the assembly comprising: a biasing member being compressible between a relaxed position and a compressed position along the linear path of the switch; wherein the biasing member at least partially surrounds the switch; and wherein a linear moving distance between the relaxed position of the biasing member and the compressed position of the biasing member is longer than a linear moving distance between the open position of the switch and the closed position of the switch.

41. The assembly for a medicament delivery device according to clause 39, wherein the biasing member is a compression coil spring; and wherein the switch is surrounded by the compression coil spring.

42. The assembly for a medicament delivery device according to any one of clause 38-41, wherein the linear path of the switch is in the direction of the longitudinal axis.

43. A medicament delivery device comprising the assembly according to any one of the preceding clauses.

44. The medicament delivery device according to clause 43, wherein the medicament delivery device comprises a collapsible medicament container arranged within the interior chamber of the container holder.

45. The medicament delivery device according to clause 43 or 44, comprising an outer shell extending along the longitudinal axis between a proximal end and a distal end; wherein the container holder is arranged within the outer shell.

46. The medicament delivery device according to any one of clause 43-45, wherein the actuator is arranged within the outer shell.

47. The medicament delivery device according to any one of clause 43-46, comprising a delivery member guard at least partially arranged within the outer shell; wherein the delivery member guard comprises a tubular body defining a central passage extending along the longitudinal axis, wherein the tubular body is for surrounding a delivery member connected to the medicament container.

48. The medicament delivery device according to clause 47, wherein the delivery member guard comprises two buttons arranged on the tubular body of the delivery member guard and aligned coaxially to one another in the direction of the transverse axis; wherein two buttons are movable relative to the outer shell in the direction of the transverse axis between a relaxed position and a pressed position where the two buttons are closer to each other in the direction of the transverse axis in the pressed position than in the relaxed position.

49. The medicament delivery device according to clause 48, wherein each button of the two buttons comprises a blade fixed to the button, the two blades facing towards each other in the direction of the transverse axis; and wherein when the two buttons are in the pressed position the blades are positioned closer to the longitudinal axis than when the two buttons are in the relaxed position.

50. The medicament delivery device according to clause 48 or 49, wherein the delivery member guard comprises two biasing elements respectively arranged between each button and the tubular body of the delivery member guard; and wherein the biasing elements are compressible in the direction of the transverse axis between the relaxed position of the two buttons and the pressed position of the two buttons.

51. The medicament delivery device according to clause 50, wherein the biasing elements are compression coil springs.

52. The medicament delivery device according to any one of clause 48-51, wherein the delivery member guard is movable along the longitudinal axis relative to the outer shell between an extended position where the two buttons protrude completely from the proximal end of the outer shell in the direction of the longitudinal axis and a retracted position where the two buttons at least partially received within a proximal portion of the outer shell.

53. The medicament delivery device according to clause 52, wherein a transversely linear distance between the two buttons when the two buttons are in the relaxed position defines a first length; wherein a transversely linear distance between two buttons when the two buttons are in the pressed position defines a second length; and wherein a transversely measured length of the proximal portion of the outer shell is smaller than the first length and greater than the second length.

54. A method of operating an assembly for a medicament delivery device according to any one of clause 1-42, the method comprising the steps of:

placing a medicament container within the interior chamber of the container holder;

moving the actuator along the longitudinal axis relative to the body of the medicament container;

moving the rod along the transverse axis relative to the body of the medicament container upon moving the actuator.

55. The method of operating an assembly for a medicament delivery device according to clause 53, wherein the step of placing a medicament container within the interior chamber of the container holder further comprises the steps of:

inserting the medicament container from the proximal end of the body of the container holder; and moving the medicament container axially along the longitudinal axis towards the distal end of the body of the container holder.

56. The method of operating an assembly for a medicament delivery device according to clause 54 or 55 when dependent on any one of clause 38-42, comprising the step of:

moving the switch from the open position to the closed position upon placing a medicament container within the interior chamber of the container holder.

57. The method of operating an assembly for a medicament delivery device according to clause 56 when dependent on any one of clauses 41-42, comprising the steps of:

compressing the biasing member from the relaxed position to the compressed position upon placing a medicament container within the interior chamber of the container holder; and moving the switch from the open position to the closed position.

58. An assembly for a medicament delivery device comprising:

a container holder comprising a body extending along a longitudinal axis between a proximal end and a distal end, the body defining an interior chamber for receiving a medicament container;

an actuator movable in the direction of the longitudinal axis relative the body of the container holder;

a drive assembly attached to the body of the container holder;

wherein the drive assembly comprises a motion converter and a rod movable along a transverse axis transverse to the longitudinal axis relative to the body of the container holder; and wherein the actuator comprises an activation surface configured to interact with the motion converter of the drive assembly when the actuator moves relative to the container holder in the direction of the longitudinal axis so that the rod is moved along the transverse axis.

59. A method of operating an assembly for a medicament delivery device, the assembly comprising a container holder comprising a body for receiving a medicament container; an actuator movable along a longitudinal axis relative to the body of the container holder; and a drive assembly attached to the body of the container holder; wherein the drive assembly comprises a transversely movable rod and a motion converter; the method comprising the steps of:

placing a medicament container within the body of the container holder;

moving the actuator along the longitudinal axis relative to the body of the medicament container;

moving the rod along the transverse axis relative to the body of the medicament container upon moving the actuator.

The invention claimed is:

1. An assembly for a medicament delivery device, the assembly comprising:

a container holder comprising a body extending along a longitudinal axis between a proximal and a distal end, the body defining an interior chamber for receiving a medicament container;

an actuator connected to the container holder and axially movable relative to the body of the container holder; and a drive assembly attached to the body of the container holder;

wherein the drive assembly comprises a motion converter and a rod;

wherein the actuator comprises an activation surface movable relative to the motion converter of the drive assembly in the direction of the longitudinal axis; and wherein a movement of the actuator relative to the container holder in the direction of the longitudinal axis is converted to a movement of the rod relative to the container holder along a transverse axis transverse to the longitudinal axis through an engagement between the motion converter of the drive assembly and the activation surface of the actuator; and wherein the motion converter of the drive assembly comprises a rotator fixed to the body of the container holder in the direction of the transverse axis and rotatable around the transverse axis relative to the body of the container holder; and wherein the rotator comprises a body comprising an outer surface.

2. The assembly for a medicament delivery device according to claim 1, wherein the rotator comprises teeth extending outwardly relative to the transverse axis from the outer surface of the body of the rotator; wherein the activation surface of the actuator comprises a rack; wherein each tooth of the rack extends in a direction perpendicular to the longitudinal axis; and wherein the rack aligns with the teeth of the rotator in the direction of the longitudinal axis.

3. The assembly for a medicament delivery device according to claim 2, wherein the rotator comprises an engaging member on a surface of the body of the rotator; wherein the rod comprises a first engaging member engaged with the engaging member of the rotator thereby defining a first interface; wherein the rod comprises a second engaging member engaged with a counter engaging member of the body of the container holder thereby defining a second interface; and wherein one of the first interface and the second interface is a helical interface; and the other one of the first interface and the second interface is a spline interface.

4. The assembly for a medicament delivery device according to claim 3, wherein the first interface is a helical interface.

5. The assembly for a medicament delivery device according to claim 3, wherein the second engaging member of the rod is a rib.

6. The assembly for a medicament delivery device according to claim 3, wherein the counter engaging member arranged on the body of the container holder is a rib.

7. The assembly for a medicament delivery device according to claim 1, wherein the body of the rotator is ring-shaped or tubular.

8. The assembly for a medicament delivery device according to claim 7 when dependent on claim 3, wherein the engaging member of the rotator is arranged on an inner surface of the body of the rotator.

9. The assembly for a medicament delivery device according to claim 1, wherein the rod comprises a rod body extending along the transverse axis.

10. The assembly for a medicament delivery device according to claim 3, wherein the drive assembly comprises a rotator fixed to the body of the container holder, where the body of the rotator is ring-shaped or tubular and where the body of the rotator at least partially encloses the rod body; and wherein the first engaging member of the rod is arranged on an outer surface of the rod body.

11. The assembly for a medicament delivery device according to claim 10, wherein the second engaging member of the rod is arranged on an outer surface of the rod body.

12. The assembly for a medicament delivery device according to claim 1, the assembly comprising: two drive assemblies aligned coaxially to one another in the direction of the transverse axis on the body of the container holder; wherein the actuator comprises two activation surfaces; wherein the movement of the actuator relative to the container holder in the direction of the longitudinal axis moves each rod of the two drive assemblies in the direction of the transverse axis through the engagement between one motion converter of the two drive assemblies and one activation surface of the actuator; and the engagement between the other one motion converter of the two drive assemblies and the other one activation surface of the actuator.

13. The assembly for a medicament delivery device according to claim 1, the assembly comprising: a motor connected to the actuator and a switch attached to the container holder; wherein the switch is movable relative to the body of the container holder between an open position and a closed position where the motor is configured to initiate the movement of the actuator relative to the body of the container holder.

* * * * *